(12) United States Patent
Marrot et al.

(10) Patent No.: US 9,040,103 B2
(45) Date of Patent: *May 26, 2015

(54) USE OF ESSENTIAL OIL OF OREGANO AND OF ROSEWOOD, OR CONSTITUENTS THEREOF, IN THE THERAPEUTIC TREATMENT OF KERATOSES

(75) Inventors: Laurent Marrot, Livry Gargan (FR); Jérémie Soeur, Bourg la Reine (FR); Meng-Er Huang, Orsay (FR)

(73) Assignees: L'Oreal, Paris (FR); Institut Curie, Paris (FR); Centre National de la Recherche Scientifique, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/581,015

(22) PCT Filed: Feb. 28, 2011

(86) PCT No.: PCT/FR2011/050411
§ 371 (c)(1),
(2), (4) Date: Nov. 19, 2012

(87) PCT Pub. No.: WO2011/104490
PCT Pub. Date: Sep. 1, 2011

(65) Prior Publication Data
US 2013/0059921 A1    Mar. 7, 2013

Related U.S. Application Data

(60) Provisional application No. 61/282,751, filed on Mar. 26, 2010.

(30) Foreign Application Priority Data

Feb. 26, 2010 (FR) ..................... 10 00800

(51) Int. Cl.
*A61K 36/00* (2006.01)
*A61K 36/53* (2006.01)
*A61K 31/045* (2006.01)
*A61K 36/54* (2006.01)

(52) U.S. Cl.
CPC ............. *A61K 36/53* (2013.01); *A61K 31/045* (2013.01); *A61K 36/54* (2013.01)

(58) Field of Classification Search
CPC .......................... A61K 36/53; A61K 31/045
USPC ................... 424/725, 745, 779; 514/724
See application file for complete search history.

(56) References Cited

U.S. PATENT DOCUMENTS

2008/0213410 A1    9/2008  Serrano
2008/0233218 A1    9/2008  Newmark et al.

FOREIGN PATENT DOCUMENTS

FR    2 830 198    4/2003

OTHER PUBLICATIONS

French Search Report mailed on Jul. 27, 2010, issued in corresponding French Patent Application No. 733040.
French Opinion issued in corresponding French Patent No. 1000800 (no issue date on document).
International Search Report mailed on Jan. 26, 2012, in corresponding PCT Application PCT/FR2011/050411.
Preliminary International Search Report issued on Sep. 4, 2012, in corresponding PCT Application PCT/FR2011/050411.
F. Bakkali et al., *Antigenotoxic effects of three essential oils in diploid yeast (Saccharomyces cerevisiae) after treatments with UVC radiation, 8-MOP plus UVA and MMS*, 606 Mutation Research 27-38 (2006).
S. Bouhdid et al., *Antibacterial and antioxidant activities of Origanum compactum essential oil*, 7(10) African Journal of Biotechnology 1563-1570 (May 16, 2008).
A. Calcabrini et al., *Terpinen-4-ol, The Main Component of Melaleuca Alternifolia (Tea Tree) Oil Inhibits the In Vitro Growth of Human Melanoma Cells*, 122 J. Invest Dermatol 349-360 (2004).
J. Cleaver et al., *UV Damage, DNA Repair and Skin Carcinogenesis* 7 Frontiers in Bioscience d1024-1043 (Apr. 1, 2002).
C. Diaz, et al., *Chemical composition of Schinus molle essential oil and its cytotoxic activity on tumour cell lines*, 22(17) Natural Product Research 1521-1534 (Nov. 20, 2008).
C. Dwivedi et al., *Chemopreventive Effects of α-Santalol on Skin tumor Development in CD-1 and SENCAR Mice*, 12 Cancer Epidemiology, Biomarkers & Prevention 151-156 (Feb. 2003).
C. Dwivedi et al., *Chemopreventive effects of sandalwood oil on skin papillomas in mice*, 6 European Journal of Cancer Prevention 399-401 (1997).
J. Einspahr et al., *Expression of p53 Protein in Actinic Keratosis, Adjacent, Normal-appearing, and Non-Sun-exposed Human Skin* 6 Cancer Epidemiology, Biomarkers & Prevention 583-587 (Aug. 1997).

(Continued)

*Primary Examiner* — Kevin E Weddington
(74) *Attorney, Agent, or Firm* — Buchanan Ingersoll & Rooney PC

(57) ABSTRACT

The present invention concerns various compositions comprising the essential oil of *Origanum compactum* or of *Aniba rosaeodora* or one of their constituents, preferably a major constituent, for use in the targeted treatment and prevention of keratoses in the transformation phase and of carcinomas originating from these keratoses, and more particularly of keratoses induced by solar radiation on the skin of a subject. More particularly, the present invention concerns compositions based on the essential oil of oregano or of rosewood, or on linalool, thymol or carvacrol.

18 Claims, 7 Drawing Sheets

(56) References Cited

OTHER PUBLICATIONS

W. Erhardt, Zander—*Andwörterbuch de Pflanzennamen*—16 Eugen Ulmer, Stuttgart 556-557 (2000).

N. Fusenig et al., Multiple Stages and Genetic Alterations in Immortalization, Malignant Transformation, and Tumor Progression of Human Skin Keratinocytes, 23 Molecular Carcinogenesis 144-158 (1998).

V. Gogvadze et al., *Mitochondria in cancer cells: what is so special about them?*, 18(4) Trends in Cell Biology 165-173 (2008).

A. Itharat et al., *In vitro cytotoxic activity of Thai medicinal plants used traditionally to treat cancer*, 90 Journal of Ethnopharmacology 33-38 (2004).

M. Kaur et al., *Skin cancer chemopreventive agent, α-santalol, induces apoptotic death of human epidermoid carcinoma A431 cells caspase activation together with dissipation of mitochondrial membrane potential an cytochrome c release*, 26(2) Carcinogenesis 369-380 (2005).

K. Koba et al., *Chemical Composition and in vitro Cytotoxic Activity of Essential Oils from Two Tropical Lamiaceae: Aeollanthus pubescens Benth. and Ocimum gratissimum L.*, 10(1) Jeobp 60-69 (2007).

Koba et al., *In vitro cytotoxic activity of Cymbopogon citratus L. and Cymbopogon nardus L. essential oils from Togo*, 4 Bangladesh J. Pharmacol 39-34 (2009).

D. Kulms et al., *Molecular mechanisms of UV-induced apoptosis*, 16 Photodermatol Photoimmunol Photomed 195-201 (2000).

A. Kumar et al., *An essential oil and its major constituent isointermedeol induced apoptosis by increased expression of mitochondrial cytochrome c and apical death receptors in human leukaemia HL-60 cells*, 171 Chemico-Biological Interactions 332-347 (2008).

M. Loizzo et al., *Antiproliferative effects of essential oils and their major constituents in human renal adenocarcinoma and amelanotic melanoma cells*, 41 Cell Profil. 1002-1012 (2008).

L. Marrot et al., *Skin DNA photodamage and its biological consequences*, 58(5) J. Am Acad Dermatol S139-S148 (May 2008).

A. Molassiotis et al., *Use of complementary and alternative medicine in cancer patients: a European survey*, 16 Annals of Oncology 655-663 (2005).

A. Mudgil et al., *Ultraviolet B Irradiation Induces Expansion of Intraepithelial Tumor Cells in a Tissue Model of Early Cancer Progression*, 121(1) The Journal of Investigative Dermatology 191-197 (2003).

J-P. Ortonne, *From actinic keratosis to squamous cell carcinoma*, 146(Suppl. 61) British Journal of Dermatology 20-23 (2002).

P. Sharma et al., *Anticancer activity of an essential oil from Cymbopogon flexuosus*, 179 Chemico-Biological Interactions 160-168 (2009).

M. Taguchi et al., *Aberrations of the Tumor Suppressor p53 Gene and p53 Protein in Solar Keratosis in Human Skin*, 103(4) The Journal of Investigative Dermatology 500-503 (Oct. 1994).

X. Tang et al., *CP-31398 restores mutant p53 tumor suppressor function and inhibits UVB-induced skin carcinogenesis in mice*, 117(12) The Journal of Clinical Investigation 3753-3764 (Dec. 2007).

M. Verma et al., *Induction of Mitochondrial-Dependent Apoptosis by an Essential Oil from Tanacetum gracile*, 74 Planta Med 515-520 (2008).

K. Wischermann et al., *UVA radiation causes DNA strand breaks, chromosomal aberrations and tumorigenic transformation in HaCaT skin keratinocytes*, 27 Oncogene 4269-4280 (2008).

Welcome to the Victorian Garden of the 1800s . . . URL:http://webcache.googleusercontent.com/search?q=cache:z0dC1BbW9d0J:www.thevictoriangarden.co.za/Al_FacialProducts_pop-up.htm+site:http://www.thevictoriangarden.co.za/Al_FacialProducts_pop-up.htm&cd=1&hl=en&ct=clnk&gl=de&tob=1 pp. 1-8 (Jun. 25, 2010).

Avocado Oil, URL:http://web.archive.org/web/20080614124629/http://www.naturesgift.com/carrier_oils/avocadoOil.htm pp. 1-2 (Jun. 14, 2008).

FAQ URL:http://web.archive.org/web/20070806205742/http://www.wildoiloforegano.com/index.php?page=faq pp. 1-7 (Aug. 6, 2007).

Testimonials URL:http://web.archive.org/web/20070806205829/http://wildoiloforegano.com/index.php?page=testimonials> pp. 1-7 (Aug. 6, 2007).

Price List and Order Form URL:http://web.archive.org/web/20080322083726/http://www.thevictoriangarden.co.za/PriceOrder.html> pp. 1-6 (Mar. 22, 2008).

Personal Body, Care, Baby, Care, Cosmetics—Ingredients URL:http://www.earthorigin.co.za.ingredients.html> pp. 52-106 (May 11, 2009).

Seborrheic Keratosis—at Home Treatment URL:http://www.essentialdayspa.com/forum/viewthread.php?tid=30365&start=375> pp. 1-9 (Feb. 6, 2010).

Skin Cancer Forum—wild oregano oil—skin cancer testimonies URL:http://www.topicalinfo.or/forum/topic.asp?TOPIC_ID=308> (May 26, 2008)

Keratosis pilaris URL:http://www.wildrafted.com.au/Articles/Natural_Skin_Care_Articles/Keratosis_pilaris.html> pp. 1-5.(Dec. 28, 2009).

Wild Oil of Oregano http:www.oiloforegano.com/oil-of-oregano-research-article-3.html.

Welcome to Pure Healing Europe: Herpes Treatments and Warts URL:http://www.purehealing-eu.com/body-warts/treatment-body-warts.htm> (Nov. 21, 2009).

Knight et al., *Cooperation between Different Forms of the Human Papillomavirus Type 1 E4 Protein to Block Cell Cycle Progression and Cellular DNA Synthesis*, 78(24) Journal of Virology 13920-13933 (Dec. 2004).

Naylor, *Cutaneous Human Papillomavirus Infections*, pp. 1-31 http://www.archive.orq/web/20090305073730/http://www.telemedicine.ord/warts/cutmanhpv.htm (Mar. 5, 2009).

European Office Action issued in related EP Patent No. 11 713 498.1-1456 mailed on Jan. 26, 2015.

USE OF ESSENTIAL OIL OF OREGANO AND OF ROSEWOOD, OR CONSTITUENTS THEREOF, IN THE THERAPEUTIC TREATMENT OF KERATOSES

CROSS-REFERENCE TO RELATED APPLICATIONS

This application is a U.S. National Stage patent application pursuant to 35 U.S.C. §371 of International Patent Application PCT/FR2011/050411, filed on Feb. 28, 2011, and published as WO 2011/104490 on Sep. 1, 2011, which claims priority to U.S. Provisional Patent Application Ser. No. 61/282,751, filed on Mar. 26, 2010, and French patent application Ser. No. 10/00800, filed on Feb. 26, 2010, all of which are incorporated herein by reference in their entireties for all purposes.

The present invention relates to the field of the prevention and targeted therapeutic treatment of actinic keratoses.

Solar radiation is a proven cause of the development of skin cancers, in particular spino-cellular carcinomas (SC) and baso-cellular carcinomas (BCC) involving keratinocytes (Cleaver, J. E. et al, 2002). The ultraviolet region (300-400 nm) is primarily involved in this process, with UVB (300-320 nm) having the major impact, although even UVA contributes to increasing the risk. It is clearly established in the literature that solar UV induces lesions in the DNA of the genome of epidermal cells, in particular the pyrimidine dimers. This damage, if not repaired correctly, is a source of mutations that constitute the first step towards tumorigenesis (Margot L. et al, 2008).

The p53 protein plays a very important role in skin homeostasis, in particular as regards control of the cell cycle. When DNA lesions are induced, p53 is modified by various phosphorylations (principally on serine 15) that activate it as a transcription factor. If the level of damage is acceptable, p53 can arrest the cell cycle at the G0/G1 phase and stimulate the repair functions of the DNA. In contrast, if the genomic material is altered too much, p53 promotes the triggering of apoptosis, thereby eliminating the cells at risk (Kulms D. et al, 2000).

The gene coding for the p53 protein is frequently damaged by UV and in some cases is subjected to mutations, in particular CC to TT mutations. Cells that are mutated thereby may lose the specific response to UV controlled by the p53 protein: thus, repair is less effective and the presence of damage to the DNA no longer arrests proliferation: replication can occur in the presence of lesions, thereby increasing the risk of errors (mutations), leading in time to high genetic instability. Since mutated cells enter the apoptosis process less easily, they finish up by manifesting a growth advantage compared with normal cells. This process of clonal expansion of abnormal cells creates pre-cancerous patches in the affected organs (Brash, D. E., 2006).

Apoptosis is a complex process which may have various origins, but it is currently accepted that mitochondria play an important role therein. Various molecular signals, such as the Bcl2/Bax equilibrium, for example, possibly competing with p53, are capable of modifying the permeability of the mitochondrial membrane and of promoting release of cytochrome C into the cytosol. That process may initiate activation of the caspase pathway, caspases being the enzymes in charge of the degradation of certain intracellular compounds, which irreversibly results in apoptosis (Gogvadze et al., 2008). Further, it has also been demonstrated that permeabilization of the mitochondrial membrane can release various pro-oxidizing mitochondrial molecules into the cytosol, allowing the induction of apoptosis.

In the skin, it has been shown that keratoses and carcinomas are frequently constituted by keratinocytes carrying a mutation in the p53 gene (Taguchi, M. et al. 1994).

In addition, analysis of the sequences where such mutations occur shows that they very frequently correspond to sites that are favorable to the formation of pyrimidine dimers.

Dermatologically, keratoses appear as zones of epithelial dysplasia which are observed in regions of the body that are frequently exposed to the sun, and are often associated with photo-aging. Between 1% and 10% of such keratoses can become cancerous, with the development of squamous SCC carcinomas; the others regress spontaneously (Ortonne, J. P. 2002).

In order to study these skin cancer mechanisms, it is possible to use keratinocytes carrying mutations in the p53 gene. This is the case with the HaCat line, which was originally described by Fusenig et al. (Fusenig, N. E. et al. 1998) and which is now very frequently employed in various dermatological research laboratories. Thus, for example, HaCat cells have been integrated into an organotypic model of the skin in the presence of normal keratinocytes: in such a system, it was possible to mimic the promoter effects of exposure to the sun by demonstrating the capacity of UVB to stimulate clonal expansion of HaCat cells (Mudgil, A. V. et al. 2003) mutated at p53. More recently, it has been reported that HaCat cells exposed to UVA and reimplanted into mice could be the source of skin tumors (Wischermann, K. et al. 2008). These data suggest that products inducing a significantly more intense cytotoxicity in HaCat cells compared with normal human keratinocytes (or keratinocyte lines not mutated at p53) could potentially be capable of treating actinic keratoses and also of reducing the risk of the development of carcinomas, in particular SCC. For this reason, the work described below consisted of comparing and understanding the cytotoxic effect of essential oils on normal human keratinocytes, on HaCat keratinocytes (carrying a mutation at p53) and on immortalized keratinocytes originating from carcinoma.

Essential oils (EO) and their derivative products are currently very popular products with consumers. This popularity, specifically for products of natural origin (agroalimentary, cosmetology, pharmacology, etc.) or arising from the "natural" concept, is the consequence of a general demand for products of a durable development type (green chemistry, bio-agriculture). This interest in "nature" and its "soft medicine" products (aromatherapy, phytotherapy) also has its origin in the limitations of conventional medicine (viral resistance, bacterial resistance, cancer treatment, etc.). The absence of substantial secondary effects in the context of well-documented, reasoned aromatherapy treatments is a major advantage in the use of essential oils.

Essential oils are complex, volatile products with a powerful odor, characteristic of the part of the plant used for its manufacture. Of approximately 800000 recorded plant species, only aromatic plants are used to obtain essential oils. These are plants with sufficient cells synthesizing and secreting those aromatic molecules, i.e. approximately 3000 plants of biological interest. The major portion of the essential oils on the market is represented by approximately 300 essential oils.

Essential oils correspond to a complex mixture of secondary metabolites (molecules not essential to survival of the plant) synthesized and secreted by specialized organs: epidermal glandular hairs, glandular pouches and channels (schizogens or schizolysigens). Such secondary metabolites are represented by a very wide diversity of chemical molecules. The most common are terpenes (mono-, sesqui- and diterpene: C10, C15 and C20 respectively) and other aromatic molecules (cyclic molecules). All chemical functions are present in the essential oils: aldehydes, ketones, alcohols, peroxides, lactones, ethers, esters, etc.

Essential oils are obtained after hydro-distillation of plant material of the aromatic plant. Currently, various extraction methods are used; examples that may be cited are supercritical $CO_2$ extraction and solvent extraction.

Essential oils have a recognized cosmetic and therapeutic potential and are principally used for their bactericidal, virucidal, antioxidant and anti-inflammatory activities, but also for their fragrant character, which is capable of causing a feeling of well-being. Several modes of using essential oils are possible: inhalation, ingestion or application to the skin. Pure essential oils are almost never applied directly to the skin as they are often irritants, but are diluted in other vegetable oils (olive oil, sunflower seed oil, etc.). Application to the skin is carried out in the context of massage, local treatments (infections) or when using perfumes (major constituents).

In addition to their cosmetic interest, essential oils are also used in the context of certain antibiotic treatments for their ability to enhance their efficiency, or to combat infections of the respiratory tracts. In the same manner, a non-negligible proportion (approximately 35%) of European patients with cancer for whom conventional treatment has not provided a cure have turned to complementary methods such as aromatherapy as an alternative to conventional medicine (Molassiotis, A. et al. 2005). Some studies have demonstrated the anticancer and/or antiproliferative properties of essential oils as regards certain cancer lines. Thus, recent work has demonstrated potentially anti-carcinogenic or antiproliferative activities of certain essential oils on leukemia cell lines (Kumar, A. et al. 2008), (Verma, M. et al. 2008), colon cancer lines (Sharma, P. R. et al. 2008), breast cancer cells (Diaz, C. et al. 2008), or melanoma cells (Loizzo, M. R. et al. 2008).

Other studies have also demonstrated an antiproliferative activity of certain compounds isolated from essential oils, such as alpha santalol on an epidermoid carcinoma line (Kaur, M. et al, 2005), or that of terpinee-4-ol, from the essential oil of tea tree, on melanoma cells (Calcabrini, A. et al. 2004).

Regarding keratinocytes, the cytotoxicity of certain essential oils has been studied as regards the keratinocyte line HaCat mutated at p53 (Koba K. et al. 2009) or of the keratinocyte line SVK14 (Itharat, A. et al. 2004).

In general, the invention concerns any composition comprising at least one of the constituents of the essential oil of *Origanum compactum* or of the essential oil of *Aniba rosaeodora*, for a therapeutic use in the prevention or treatment, preferably targeted, of keratoses in the transformation phase, of keratoses presenting tumor cells, of pre-cancerous or cancerous keratinocytes, or of carcinoma originating from the transformation of keratoses, and more specifically of actinic keratoses.

More particularly, the invention concerns the essential oil extracted from different parts (roots, stems, bark, leaves) of *Origanum compactum* or of *Aniba rosaeodora* as well as any essential oil containing at least one of the compounds identified in the essential oils of compact oregano and of rosewood, preferably linalool, thymol and/or carvacrol.

The present inventors have surprisingly demonstrated that the essential oil from compact oregano (*Origanum compactum*, Lamiaceae family) and the essential oil from rosewood (*Aniba rosaeodora*, Lauraceae family) can induce cell death by apoptosis in a targeted manner in cancerous human keratinocytes and pre-cancerous keratinocytes mutated at p53 compared with normal keratinocytes. The inventors have also demonstrated that the targeted cytotoxic effect is present with the major constituents of these essential oils even in the absence of the other constituents.

In accordance with the present invention, any composition containing the essential oil of compact oregano or of rosewood, or containing at least one of their constituents, preferably a preponderant constituent, may thus be used to prevent, treat and reduce keratoses known to be formed very often from keratinocytes carrying mutations in the p53 gene induced by UV, more particularly to treat keratosis in the transformation phase, pre-cancerous and cancerous keratinocytes or carcinomas deriving from the transformation of keratoses. This treatment also has the advantage of not generating inflammation, since apoptosis is not a pro-inflammatory process.

More specifically, the invention concerns various therapeutic applications of compositions comprising the essential oil of *Origanum compactum* or of *Aniba rosaeodora*, or comprising at least one of their constituents, in particular other essential oils having constituents in common with the essential oil of *Origanum compactum* or of *Aniba rosaeodora* in the prevention or treatment of keratosis, more particularly keratoses in the transformation phase, pre-cancerous, or cancerous, in particular skin carcinomas, preferably UV-induced. The various therapeutic applications of the invention are preferably for human beings.

The expression "prophylactic or therapeutic applications" as used in the present invention means treatments aimed at preserving or restoring the health of a patient, and not treatments with a purely esthetic or cosmetic purpose.

In the context of the present invention, the compositions under consideration are for use in the treatment or the prevention of keratoses in the transformation phase. Such keratoses to be treated contain tumor cells or potential tumor cells. In this situation, a physician would recommend excision of the keratoses for therapeutic reasons, given that it would probably or certainly develop into a carcinoma. The keratoses under consideration are preferably large in size and in particular are at great risk of turning cancerous in the short or medium term.

The present invention also concerns compositions for use in the treatment or the prevention of the appearance of cancerous keratinocytes or of carcinoma deriving from the transformation of keratosis, in particular UV-induced skin carcinomas.

The invention also consists in the use of the compositions under consideration for the manufacture of a drug for the treatment or prevention of keratoses in the transformation phase or for the treatment or the prevention of the appearance of pre-cancerous or cancerous keratinocytes or of carcinoma originating from the transformation of keratoses. The invention also concerns the use of the essential oil of *Origanum compactum* or of *Aniba rosaeodora* or of at least one of their constituents, preferably major, for the manufacture of a drug for the treatment or the prevention of keratoses in the transformation phase, of pre-cancerous or cancerous keratinocytes or of carcinoma originating from the transformation of keratosis.

The term "keratosis" (or keratoderma or hyperkeratosis) means a hyperplasia of the epidermal stratum corneum. The term "actinic keratosis" or "solar keratosis" means a keratosis induced by exposure to solar radiation. In the context of the present invention, keratoses that are particular preferred for therapeutic applications are actinic keratoses. Preferably, the keratoses under consideration are constituted by or mainly comprise cells mutated at p53.

Because they have been occurring more and more frequently over the past decades, there is in fact a significant need for the prevention and/or treatment of keratoses in the transformation phase, presenting a danger of becoming cancerous, and of carcinomas originating from such keratoses.

Thus, the invention concerns a composition comprising the essential oil of rosewood or of compact oregano or comprising at least one of their constituents, or comprising an essential oil having at least one constituent in common with the essential oil of rosewood or of compact oregano, for use in the prevention or targeted therapeutic treatment of keratoses in the transformation phase, of cancerous keratinocytes or of carcinoma originating from the transformation of keratoses. Preferably, it is a major constituent of the essential oil of *Origanum compactum* or of *Aniba rosaeodora*.

The expression "major constituent" or "preponderant constituent" of an essential oil means either a constituent the proportion of which in that essential oil is more than 10% by weight, or one of the five constituents the proportion by weight of which is the highest in that essential oil. Preferably, in the context of the present invention, a "major or preponderant constituent" means one of the five most abundant constituents, by weight, in the essential oil.

The expression "prevention of keratoses in the transformation phase, of pre-cancerous or cancerous keratinocytes or of carcinomas originating from the transformation of keratoses" in particular means obtaining a preventative effect such that the keratoses do not transform, or do not progress towards a cancerous stage.

The expression "treatment of keratoses in the transformation phase, of cancerous keratinocytes or of carcinomas originating from the transformation of keratoses" in particular means an effect such that cancerous keratoses or keratoses in the transformation phase that already exist stop growing and regress or even disappear entirely, or return to a non-cancerous stage, or the number of cancerous cells or cells in the transformation phase is reduced.

The prevention or treatment of keratoses is particularly appropriate in the case of skin that has been exposed to a strong UV radiation or to repeated exposure to UV. These situations are in fact likely to produce mutations in p53, the development of keratoses and their change into a cancerous stage.

The prevention or treatment of cancerous keratoses or keratoses in the transformation phase in a therapeutic application of the invention is also particularly appropriate in the case of keratoses in the development phase, i.e. the keratoses are already present on the skin and that they are growing. During this process, the risk of moving into a cancerous stage is in fact increased. In such a situation, the compositions for therapeutic use of the invention can be used to reduce the risk of transformation into a cancerous stage.

One of the major advantages of the described compositions for therapeutic use lies in the targeted action of the essential oils of *Origanum compactum* or of *Aniba rosaeodora* and of their constituents. In fact, the essential oil of *Origanum compactum* and that of *Aniba rosaeodora*, or at least one of their constituents has, in one range of concentration, a targeted action against pre-cancerous and cancerous cells (mutated at p53) that may be hyperproliferative; normal cells are hardly affected by the cytotoxicity. It is thus possible to treat all of the skin of an individual without any deleterious effect for the normal keratinocytes. This property is particularly appreciated in the context of a treatment, as it can thus avoid the secondary effects linked to the therapy, namely, the toxicity of this treatment as regards normal cells, in particular normal keratinocytes, around the zones to be treated, is low.

It should be noted that the inventors are in fact the first to have carried out a comparative study of the impacts of essential oils on keratinocytes mutated at p53 and on normal keratinocytes. No data relating to such a comparison of cytotoxicity had been available before the present invention. The targeted action of the essential oils and their constituents thus had never been brought to light before the invention. In view of the foregoing, then, the present invention can be used for the prevention or targeted treatment of cancerous keratoses or keratoses in the transformation phase.

The term "targeted cytotoxicity" as used in the invention means that the property of cytotoxicity is preferentially induced in hyperproliferative cells and/or p53-mutated cells (for example HaCat and A431) compared with non-hyperproliferative cells, not mutated at p53 (for example HEK001 or NHEK894), i.e. the toxicity levels are at least 1.5 times higher in mutated cells than in non-mutated cells, preferably at least 2 times higher. Preferably, the viability of the non-hyperproliferative, non-mutated cells remains of the order of at least 40%, or even 50%, preferably 60%. The inventors have demonstrated the existence of ranges of concentrations for which such a targeted cytotoxicity, saving the healthy cells, in particular normal non-cancerous keratinocytes, could be obtained.

This targeted action can also be used to envisage repeated applications because the compositions present no danger to healthy cells.

In the compositions of the present invention, the essential oil under consideration or the constituent of the essential oil under consideration constitutes the active principle of the composition or one of the active principles, because the inventors have demonstrated the targeted cytotoxicity of the essential oils and of their constituents against mutated keratinocytes In accordance with a preferred embodiment of the present invention, the composition contains at least one of the constituents of the essential oil of *Origanum compactum* or of *Aniba rosaeodora*; preferably, it comprises at least 10%, or at least 15% or 20% by weight of linalool, carvacrol or thymol. Preferably, it has a composition that comprises an essential oil or a mixture of essential oils such that the mixture comprises said proportions of linalool, carvacrol or thymol. The invention also concerns compositions in which said percentages correspond to chromatographic percentages.

In the experimental section, the cytotoxicity of two essential oils has been studied in particular: the essential oil of compact oregano (*Origanum compactum*, Lamiaceae family) and the essential oil of rosewood (*Aniba rosaeodora*, Lauraceae family), on human epidermal cells: the keratinocyte line HaCat (mutated at p53 and spontaneously immortalized), the A431 line (from a spino-cellular carcinoma, mutated at p53) as well as normal human primary epidermal keratinocytes.

The essential oil of compact oregano is primarily composed of two monophenols (terpenoids): thymol and carvacrol. This essential oil is recommended in the context of the treatment of colitis and pulmonary disorders. It can combat fatigue, but it is primarily a broad spectrum bactericide.

The essential oil of rosewood is composed of 80% linalool. Its properties are used to treat irritated, fatigued and wrinkled skin. It is also anti-infectious (less powerful than the essential oil of oregano), immuno stimulating and tends to improve depressive behavior. It is very slightly irritant and slightly toxic.

The present invention preferentially concerns compositions comprising the essential oil of *Origanum compactum* and/or of *Aniba rosaeodora* or at least one of their major constituents selected from linalool, thymol and carvacrol.

Although the cytotoxic activity of an isolated constituent is less than that of a complete essential oil, in accordance with another embodiment of the invention, the composition comprises at least one constituent of the essential oil of *Origanum compactum* or of *Aniba rosaeodora*; for example, it comprises an essential oil containing at least one constituent of the essential oil of *Origanum compactum* or of *Aniba rosaeodora*.

The various constituents of the essential oils are well known to the skilled person and may be obtained from firms marketing said essential oils. Example 1 of the present application provides an analytical characterization of the various constituents detected in the essential oils of *Origanum compactum* and of *Aniba rosaeodora*. It should be noted that none of these two essential oils contains alpha-santalol.

Particularly preferably, in the context of the present invention, the constituent of one of the two cited essential oils used is not linalool oxide, and preferably not an oxide at all.

Preferably, the component used is an alcohol or a phenol, more particularly preferably a terpenol or terpenic alcohol such as linalool, terpineol, nerol, geraniol, citronellol, or menthanol, or a terpenoid such as citral, menthol, carvacrol or thymol; other terpenes that may also be envisaged are p-cymene, terpinene, myrcene and beta caryophyllene. Particularly preferred constituents are linalool, carvacrol and thymol.

In other preferred embodiments of the compositions for a therapeutic use as described above, the constituent is selected from 1,8-cineole, terpinolene, linalool, alpha-terpineol, geraniol, alpha-copaene, alpha and beta-selinene, benzyl benzoate, alpha-thujene, alpha pinene, myrcene, alpha-phellandrene, alpha terpinene, para-cymene, beta-phellandrene, gamma-terpinene, thymol, carvacrol and beta caryophyllene. They are in fact constituents of one or the other of the essential oils of oregano and of rosewood, wherein the proportion in the volatile part of the oil is more than 0.5% (as a chromatographic percentage).

In accordance with another embodiment of compositions for the therapeutic application mentioned, an essential oil is used comprising at least 0.5% by weight or as a chromatographic percentage, preferably at least 1%, or even 5% of at least one of the following compounds: 1,8-cineole, terpinolene, linalool, alpha-terpineol, geraniol, alpha-copaene, alpha and beta-selinene, benzyl benzoate, alpha-thujene, alpha pinene, myrcene, alpha-phellandrene, alpha terpinene, para-cymene, beta-phellandrene, gamma-terpinene, thymol, carvacrol and beta caryophyllene. Preferably, it is a chromatographic percentage applied to the volatile portion of the essential oil.

Particularly preferably, compositions are used comprising at least one essential oil constituent selected from the following components: linalool, thymol and carvacrol. Linalool is the major compound of the essential oil of rosewood and thymol and carvacrol are the two major compounds in the essential oil of oregano.

In a preferred embodiment for a therapeutic use as described above, the invention also concerns a composition consisting of or comprising an essential oil comprising at least one of the following constituents: linalool, thymol and carvacrol. Preferably, at least one of these components is present, in the essential oil or in the composition, in a proportion of more than 0.5%, preferably more than 1%, 5% or even 10%, 15% or 20% by weight. Alternatively, it may concern chromatographic percentages. Such an essential oil is, for example, the essential oil of thyme, wild thyme or savory (large proportion of thymol or carvacrol) or the essential oil of basil, of thyme (with linalool, *Thymus vulgaris* linaloliferum), of lavender or of Shiu wood (also known as Ho wood).

More particularly, the present invention concerns compositions for the therapeutic application mentioned, comprising at least 10%, preferably at least 15% or at least 20% of one of the following constituents: linalool, carvacrol and thymol. Other compositions that may also be envisaged are such that the cumulative quantity of linalool, carvacrol and thymol is more than 10%, preferably more than 15%, or even more than 20% by weight. Alternatively, they may be chromatographic percentages.

In accordance with another embodiment of the invention, the component of the essential oil of *Origanum compactum* or of *Aniba rosaeodora* used in the compositions for the envisaged therapeutic applications is selected from alpha pinene, camphene, myrcene, alpha terpinene, para-cymene, trans-ocimene, gamma-terpinene, linalool, terpinen-4-ol, beta caryophyllene, alpha-humulene and caryophyllene oxide. They are in fact components which are common to the two essential oils of oregano and of rosewood.

In another embodiment, the invention also concerns a composition comprising an essential oil containing at least one constituent in common with the essential oil of rosewood or of compact oregano, for therapeutic use in the treatment of keratoses. Preferably, said component is one of the following components: alpha pinene, camphene, myrcene, alpha terpinene, para-cymene, trans-ocimene, gamma-terpinene, linalool, terpinen-4-ol, beta caryophyllene, alpha-humulene or caryophyllene oxide. Preferably, at least one of these components is present in a proportion of more than 0.5%, preferably more than 1%, 5% or even 10%, 15% or 20% by weight. Alternatively, they may be chromatographic percentages.

In accordance with another embodiment envisaged in the context of the present invention, the essential oil containing a constituent in common with the essential oil of rosewood or of compact oregano is extracted from plants of the Lamiaceae or Lauraceae family.

More particularly, the essential oil having a constituent in common with the essential oil of rosewood or of compact oregano is extracted from plants originating from one of the following botanical genuses of the Lamiaceae family: *Origanum, Acinos, Agastache, Ajuga, Calamintha, Glechoma, Hyssopus, Lamium, Lavandula, Leonurus, Lycopus, Melissa, Melittis, Mentha, Micromeria, Monarda, Ocimum, Orthosiphon, Perilla, Perovskia, Phlomis, Physostegia, Pogostemon, Prostanthera, Prunella, Rosmarinus, Salvia, Satureja, Scutellaria, Sideritis, Solenostemon, Stachys, Teucrium* and *Thymus*. Preferably, it is from the genus *Origanum*.

Preferred compositions in the context of the present invention comprise an essential oil extracted from oregano, lavender, mint, rosemary, savory, sage, thyme, spotted deadnettle, black horehound, bugle weed, basil, hyssop, marjoram, deadnettle, ground ivy, wood betony, prunella, wild thyme or lemon balm.

More particularly preferably, in the therapeutic applications of the present invention, the composition comprises an essential oil or one of its constituents, preferably a major constituent, which is extracted from the species *Origanum compactum*, in particular thymol or carvacrol.

In accordance with another implementation of the invention, the essential oil having a constituent common with the essential oil of rosewood or of compact oregano is extracted from plants deriving from one of the following botanical genuses of the Lauraceae family: *Aniba, Cinnamomum, Laurus, Persea, Ravensara* or *Umbellularia*. Preferably, it is from the genus *Aniba*.

Preferred compositions in the context of the present invention comprise an essential oil extracted from rosewood, cinnamon, laurel, horseradish (Ravensara), camphor or avocado.

More particularly preferably, in the therapeutic applications of the present invention, the composition comprises an essential oil or one of its constituents, preferably major, which is extracted from the species *Aniba rosaeodora*, in particular linalool.

In accordance with another embodiment of the invention, a composition is used comprising an essential oil having a constituent in common with the essential oil of rosewood or of compact oregano or a constituent of the essential oil of rosewood or of oregano that is capable of generating a pro-oxidizing endogenous situation that is specifically produced in keratinocytes that are mutated at p53. Particular essential oils with this property are the essential oil of compact oregano and the essential oil of rosewood. Results in this regard are shown in Example 2 of the experimental section. The detailed molecular analysis in the experimental section shows that these essential oils cause destabilization of the mitochondrial membrane and release of reactive oxygen species, at the origin of the cytotoxicity targeted against pre-cancerous cells (HaCat cells) and cancerous cells (A431 cells) mutated at p53.

The examples also define simple tests for demonstrating the generation of a pro-oxidizing situation, in particular by detecting the production of the mitochondrial superoxide anion.

The essential oil or the essential oil constituent used in accordance with the invention may be extracted from roots, stems, bark or leaves of said plant. Reliable techniques are known for extracting essential oils, in particular cold extraction, which consists of placing the plant matter under high pressure using a hydraulic press, steam entrainment, which consists of forming steam that passes through the plants and picks up the aromatic molecules, and dry distillation. The essential oil obtained by distillation is a plant essence modified by oxidation and hydrolysis. A managed temperature and a low pressure are essential in conserving aromatic quality and a chemical composition as close as possible to the plant essence to be extracted. The majority of essential oils are obtained by distillation and steam entrainment (hydro-distillation).

Other extraction techniques are well known and the skilled person will know, as a function of the plant under consideration, which technique is the most appropriate. The skilled person will also know which technique is the most appropriate as a function of the part of the plant that will be used for extraction of the essential oil.

Clearly, it is preferable to use techniques that produce the highest purity and guarantee the absence of solvents in the extract obtained (essential oil or essential oil constituent).

In the context of the various therapeutic applications of the present invention, it is preferable to use compositions comprising an essential oil or an essential oil constituent in combination with other compounds. The other compounds may in particular be vegetable oils. Particularly preferred vegetable oils in combination with the essential oils of the invention or their constituents that may be cited include grapeseed oil, sweet almond oil, and also hazelnut oil, macadamia nut oil, sunflower seed oil and olive oil. In particular embodiments, the composition of the invention comprises an essential oil or essential oil constituent in combination with a sunscreen, or in combination with a moisturizing solution or a vegetable oil, or with both.

In other embodiments, the compositions of the invention may contain a combination of at least two distinct essential oils, for example an essential oil extracted from a plant of the Lamiaceae family and an essential oil extracted from a plant of the Lauraceae family.

It may also be a combination comprising an essential oil of a plant with a constituent of that same essential oil, which results in modifying the natural proportions of the various constituents of said essential oil. In particular, it may be a composition comprising the essential oil of *Origanum compactum* complemented with thymol, carvacrol and/or linalool, or a composition comprising the essential oil of *Aniba rosaeodora* also complemented with thymol, carvacrol and/or linalool.

Alternatively, it may be a combination comprising an essential oil of a plant with a constituent originating from another essential oil, extracted from a different plant, in particular the essential oil of *Origanum compactum* in association with linalool; or the essential oil of *Aniba rosaeodora* in association with thymol or carvacrol.

It may also be a composition comprising two distinct constituents, one present exclusively in the essential oil of *Origanum compactum* and the other being present exclusively in the essential oil of *Aniba rosaeodora*. As an example, the two constituents thus selected may not be together naturally in any essential oil, or not found naturally in these proportions in any essential oil.

Other additional compounds may be selected as a function of the desired texture and the desired mode of application for the compositions of the invention, for use in the treatment or the prevention of keratoses in the transformation phase, cancerous keratinocytes and carcinomas originating from the transformation of keratoses.

Furthermore in the present invention, the inventors have demonstrated the existence of a specific range of concentration of the essential oil of *Origanum compactum* and of *Aniba rosaeodora*, or of a constituent of these two essential oils for which the cytotoxicity is specifically targeted towards hyperproliferative cells and/or cells mutated at p53, as opposed to normal cells or normal keratinocytes. The therapeutic uses envisaged in the context of the present invention preferably employ a concentration range allowing targeted cytotoxicity towards cells mutated at p53 and providing a viability of at least 40%, or even at least 50% or 60% for the normal non-mutated cells. Carrying out the protocols detailed in Examples 2 and 3 of the experimental section allows the skilled person to determine the concentration ranges that are suitable for any essential oil or one of its components.

In the case of in vitro culture, the inventors have demonstrated (see Example 4) that said concentration ranges are: from 0.0125% to 0.0175% for the essential oil of oregano and from 0.035% to 0.045% for the essential oil of rosewood, in order to obtain a targeted cytotoxicity in cells mutated at p53.

As a function of this data, the skilled person will know how to adapt the composition of the invention in order to obtain a comparable concentration range. In particular, the skilled person will be able to adapt the composition of the invention into the form of a patch to guarantee a long-term contact. It is also possible to envisage repeated applications, for example every 24 h for a week or a month or more.

The various therapeutic uses in the context of the invention mean uses under conditions such that they induce a preferential cytotoxicity in cancerous or pre-cancerous keratinocytes compared with normal keratinocytes.

The invention also concerns the use of the various compositions detailed above, in particular the preferred embodiments, for the manufacture of a drug for the treatment or the prevention of keratoses in the transformation phase, cancerous or pre-cancerous keratinocytes, or of carcinoma originating from the transformation of keratoses. Said keratoses are preferably actinic keratoses.

The invention also concerns the essential oil of *Origanum compactum* or of *Aniba rosaeodora* or one of their constituents selected from thymol, carvacrol and linalool, for a therapeutic application in the human being to treat or prevent keratoses in the transformation phase, cancerous or pre-cancerous keratinocytes, carcinomas originating from the transformation of keratoses or of UV-induced carcinomas. Preferably, the keratoses are actinic keratoses. In this embodiment, the essential oil or the selected constituent forms part of the compositions described in the present invention.

In the context of this invention, the therapeutic uses mentioned are principally envisaged for topical skin applications. This is the mode of administration that not only provides the best efficacy, but also better targeting of the cells to be treated.

Other modes of administration may be envisaged, however, in particular oral, topical, intra-tumoral, enteral, parenteral, ocular, sublingual, inhaled, subcutaneous, intramuscular, intravenous, transdermal, local or rectal administration. Oral and topical forms are preferred, however. Preferably, a pharmaceutical composition is packaged in a form that is suitable for topical application, for example in the form of a patch. The term "topical application" means application to the skin and/or the mucous membranes.

A composition used in the context of the present invention comprises a concentration of the essential oil of *Origanum compactum* or of *Aniba rosaeodora* or of a constituent of these essential oils of approximately 0.03% to 0.15%, preferably approximately 0.03% to 0.1% of the essential oil of oregano, or approximately 0.06% to 0.15% of the essential oil of rosewood, for application to the skin.

The compositions of the invention generally comprise at least one pharmaceutically acceptable excipient, selected as a function of the desired pharmaceutical form and of the selected mode of administration. The formulation of the composition is adapted as a function of the selected mode of administration. For formulations with a therapeutic purpose, the following formulations may be envisaged:

For oral administration, the pharmaceutical composition may be in the form of tablets, gelules, dragees, syrups, suspensions, solutions, powders, emulsions, capsules, microspheres or nanospheres, or lipid or polymeric vesicles allowing controlled release.

For parenteral administration, the composition may be in the form of solutions or suspensions for perfusion or for injection.

For topical administration, the pharmaceutical composition of the invention is more particularly intended for the treatment of the skin and mucous membranes and may be in the form of unguents, creams, milks, pomades, powders, impregnated pads, solutions, gels, sprays, foams, lotions or sticks. It may also be in the form of suspensions of microspheres or nanospheres or lipid or polymeric vesicles or polymeric patches and hydrogels allowing controlled release. This composition for topical administration may be in the anhydrous form, in the aqueous form or in the form of an emulsion.

In the case of prophylactic uses, the compositions of the invention may be formulated into the form of a milk, for example a sun milk, in the form of a pomade or in the form of an oil.

Preferably, the essential oil selected, or one of its constituents, is formulated in combination with a vegetable oil, in particular to allow it to be diluted and thus to reduce any irritant effect.

The posology employed, the number of applications and the duration of treatment varies as a function of age, sex, the weight of the patient and the therapeutic context.

The formulation selected may be for immediate, prolonged or delayed release.

Further, since the inventors have demonstrated specific targeting of the cytotoxic effect of the essential oils of *Origanum compactum* and of *Aniba rosaeodora* and of their constituents, in particular the major constituents, against hyperproliferative cells such as cells mutated at p53, the present invention also concerns any therapeutic use of a composition comprising an essential oil of *Origanum compactum* or of *Aniba rosaeodora* or one of its constituents, preferably a major constituent, in the treatment or targeted prevention of cancerous zones of the skin due to hyperproliferation of cells of the dermis or epidermis, for example due to hyperproliferation of melanocytes, in particular in the context of melanoma.

The composition comprising the essential oil of *Origanum compactum* and/or of *Aniba rosaeodora* or one of their constituents is preferably used in combination with other compounds, in particular therapeutically and/or pharmaceutically acceptable excipients. Such pharmaceutically acceptable excipients are well known to the skilled person—they may in particular be sucrose, lactose, starch, magnesium stearate, sorbitol, gelatin, cellulose, polyethylene glycol, or indeed water, oil or alcohol, for oral liquid compositions. This list of excipients that may be used is clearly not exhaustive.

Preferably, the compositions described above are for use in the treatment of a subject suffering from a disease linked to keratoses, in particular a subject presenting keratoses in the transformation phase, pre-cancerous keratinocytes or cancerous keratinocytes or a carcinoma originating from keratosis. The carcinomas that are considered in particular in the context of the present invention are spino-cellular carcinomas (also known as epidermoid carcinomas or squamous carcinomas) and baso-cellular carcinomas.

Preferably, the keratoses, the keratinocytes or the carcinomas treated with the compositions of the invention are characterized by cells carrying mutations in the p53 protein. Not all of the cells under consideration necessarily carry a mutation in the p53 protein, but preferably at least 20% of the cells, in the keratosis or the carcinoma to be treated, carry mutations in the p53 protein, preferably at least 30%, or even at least 50% or more.

A subject who might be able to be treated using the compositions of the invention is a human being, man or woman, of any age. Preferably, it is an adult, but the invention is not limited to adults and also encompasses the treatment of adolescents, preferably over 15 years of age, for the described compositions.

Particularly preferably, the compositions mentioned above are for use in combination or in association with another treatment against keratoses, for example in association with chemotherapy, radiotherapy or dynamic phototherapy (DPT). Other treatments in combination or in association with a treatment of the invention are electrocoagulation, $CO_2$ laser treatment, liquid nitrogen application (cryotherapy), the application of a cream that modifies immunity (for example imiquimod), the application of a cream based on fluorouracil, or by electrocoagulation. Other treatments that may be envisaged concerning keratoses in the transformation phase, pre-cancerous or cancerous keratinocytes and carcinomas originating from keratosis are well known to the skilled person.

Alternations between the various types of therapy, the duration of each of them and their simultaneous or sequential use can be defined by the physician on a case by case basis depending on the patient.

It is in particular envisaged that the composition of the invention be used for the treatment of keratoses or of carcinomas before, during, after or alternating with another type of treatment against keratoses or carcinomas, in particular a treatment by chemotherapy, radiotherapy or dynamic phototherapy.

In the context of the present invention, it is also envisaged that said compositions be used to treat the skin of a patient after excision or ablation of a keratosis in the transformation phase or presenting a risk of becoming cancerous. This means that the possibility that cells that are not removed in the region surrounding the excised region could lead to the reformation of the keratosis or the carcinoma can be avoided.

The various embodiments described above may, of course, be combined together.

The present invention also concerns pharmaceutical compositions containing at least one of the constituents of the essential oil of *Origanum compactum* or of *Aniba rosaeodora*; preferably, such a composition comprises at least 10%, or at least 15% or 20%, or even at least 50% by weight of linalool, carvacrol or thymol.

The invention also concerns a composition containing linalool, carvacrol and/or thymol for use in therapy, for example a composition containing linalool and thymol or carvacrol and thymol or linalool and carvacrol or a mixture of the three, or even only one of the three. Preferably, such a composition comprises at least 10%, or at least 15% or 20% or even at least 50% by weight of linalool, carvacrol and/or thymol. The inventors have shown that the therapeutic properties of these three isolated compounds (see Example 3) justify their use as an active principle in therapeutic applications.

KEY TO FIGURES

EXPERIMENTAL SECTION

Example 1

Figure 1:
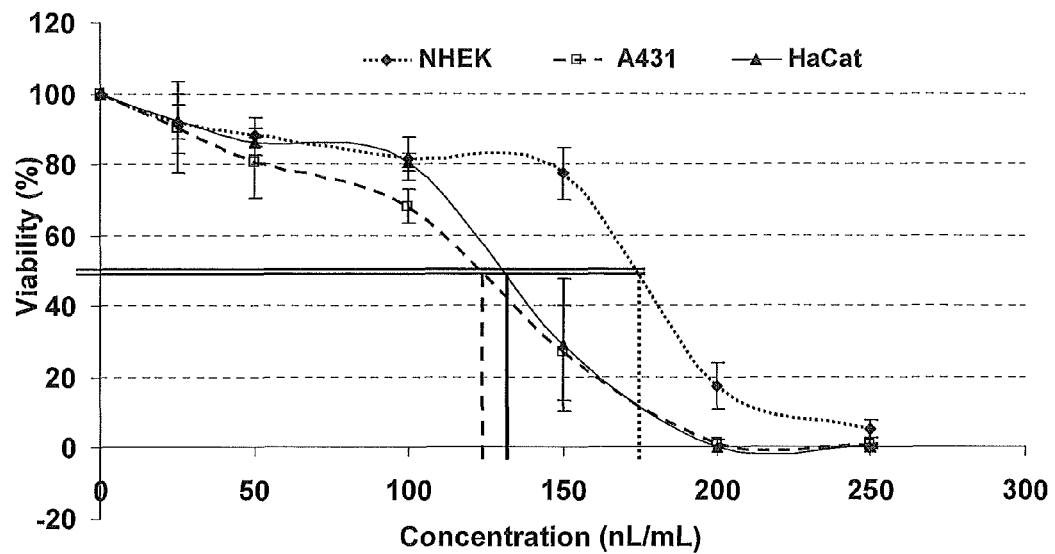
FIG. 1 represents the measurement of cell viability (MTT test) on A431, HaCat and NHEK cells treated for 4 h with the EO of oregano. The double line (═) corresponds to the 50% lethal dose (LD50)

Analytical Study of Essential Oils (EU) of Oregano and Rosewood

The choice of the EU of oregano for study was determined from the work of Dr Averbeck's laboratory, which showed an anti-genotoxic activity of this EO in yeast (Bakkali, F. et al. 2006). The EO of rosewood was selected in the light of its beneficial properties on the skin.

The present example concerns the characterization of the volatile portion of 2 commercially available bio-essential oils: an essential oil of rosewood and an essential oil of oregano.

The applied methodology involved GC-MS analysis on 2 columns with different polarities (apolar OV1 column and VF WAX polar column).

Apparatus and Methods

1. Apparatus

The analyses were carried out on Agilent instruments with 2 types of columns:
 apolar capillary column: HP-1 capillary column, length: 50 m, internal diameter: 0.2 mm, film: 0.33 μm;
 apolar capillary column: VF-WAX capillary column, length: 60 m, internal diameter: 0.25 mm, film: 0.25 μm.

It is important to emphasize that all of the percentages obtained are chromatographic percentages and not real percentages of the compounds present in the volatile phase. In order to quantify the constituents exactly, an internal standard had to be used in order to discount variations due to the instrumentation.

2. Identification of Ingredients from a Gas Chromatograph on Two Columns with Different Polarities, Coupled to a Mass Spectrometer Detector (GC/MS).

Identification of the molecules was carried out with the aid of libraries of mass spectra specific to perfumes.

The sensitivity of the instrumentation meant that compounds with a relative percentage of 0.001% or more could be quantified.

The presentation of the results and the quantification was carried out in GC/FID on an apolar column; quantification of the co-eluted constituents was carried out on a polar column.

3. Samples Analyzed
 EO of rosewood;
 EO of oregano.

Results:

Essential Oil of Rosewood:
 In light of the results, it appears that:
  99.12% of the total area of the chromatogram could be identified with certainty;
  62 molecules were identified and quantified;
  Table 1 of the composition (as chromatographic percentages) established for the essential oil of rosewood is recorded below:

TABLE 1

| ROSEWOOD | Composition %, GC |
|---|---|
| 6 METHYL 5 HEPTENE 2 ONE | 0.12 |
| LINALOYL OXIDE = LIMETOL | 0.33 |
| BETA PINENE | 0.14 |
| MYRCENE | 0.05 |
| HERBOXIDE (isomer) = DESOXYDE | 0.02 |
| BENZYL ALCOHOL | 0.01 |
| ALPHA TERPINENE | 0.02 |
| PARA-CYMENE | 0.08 |
| LIMONENE | 0.46 |
| 1,8 CINEOLE | 0.57 |
| CIS BETA OCYMENE | 0.03 |
| 5 DIMETHYL 2,2 TETRAHYDROFURAN = CITROXIDE | 0.05 |
| TRANS BETA OCIMENE | 0.09 |
| GAMMA TERPINENE | 0.02 |
| CIS LINALOOL OXIDE | 1.9 |
| TRANS LINALOOL OXIDE | 1.28 |
| TERPINOLENE | 0.52 |
| LINALOOL | 78.93 |
| HOTRIENOL | 0.2 |
| ALPHA FENCHOL | 0.02 |
| MYRCENOL | 0.06 |
| CIS OCIMENOL | 0.14 |
| NEROL OXIDE | 0.03 |
| TRANS OCIMENOL | 0.16 |
| DELTA CADINENE | 0.28 |
| TRANS NEROLIDOL | 0.27 |
| SPATHULENOL | 0.11 |
| CARYOPHYLLENE OXIDE | 0.07 |
| alcohol sesquit C15H24O HP1: 1637 | 0.23 |
| alcohol sesquit C15H24O HP1: 1646 | 0.15 |
| 7 EPI ALPHA EUDESMOL | 0.12 |
| alcohol sesquit C15H24O | 0.27 |
| EPOXY LINALOOL 1 = CIS LINALOOL OXIDE (PYRANOID) | 0.15 |
| EPOXY LINALOOL 2 = TRANS LINALOOL OXIDE (PYRANOID) | 0.25 |
| BORNEOL | 0.06 |
| TERPINEN 4 OL | 0.2 |
| ALPHA TERPINEOL | 4.52 |
| GAMMA TERPINEOL | 0.04 |
| NEROL | 0.38 |
| NERAL | 0.04 |
| GERANIOL | 1.47 |
| GERANIAL | 0.05 |
| METHYL ANISOATE | 0.02 |
| GERANYL ACETATE | 0.02 |
| ALPHA COPAENE | 1.15 |
| BETA ELEMENE | 0.13 |
| ALPHA GURJUNENE | 0.15 |
| TRANS BETA CARYOPHYLLENE | 0.04 |
| ALPHA GUAIENE | 0.05 |
| ALPHA HUMULENE | 0.02 |
| ALLO AROMADENDRENE | 0.06 |
| GAMMA MUUROLENE | 0.04 |
| SELINA 4,11 DIENE | 0.14 |
| BETA SELINENE | 0.82 |
| ALPHA SELINENE | 0.77 |
| GAMMA CADINENE | 0.12 |
| alcohol sesquit C15H24O HP1: 1689 | 0.29 |
| alcohol sesquit C15H24O HP1: 1697 | 0.4 |
| alcohol sesquit C15H24O HP1: 1701 | |
| BENZYL BENZOATE | 0.6 |
| TOTAL (%) | 99.12 | the major compound in the essential oil is linalool (78.93%);

the compounds present in the majority in the EO, after the linalool, are alpha terpineol (4.52%), linalool cis oxide (1.90%), geraniol (1.47%), trans linalool oxide (1.28%) and alpha copaene (1.15%);

the minor compound is benzyl alcohol (0.01%).

The percentages by weight of the major compounds of the essential oil of rosewood are as follows:

linalool: 78.93% alpha terpineol: 4.91%.

Essential Oil of Oregano:

In the light of the results, it appears that:

97.69% of the total area of the chromatogram could be identified with certainty;

20 molecules were identified and quantified;

Table 2 of the composition (as chromatographic percentages) established for the essential oil of oregano is below:

TABLE 2

| OREGANO | COMPOSITION % GC |
|---|---|
| Alpha thujene | 0.87 |
| Alpha pinene | 0.64 |
| Camphene | 0.12 |
| 1 octen-3-ol | 0.23 |
| Octanone 3 | 0.17 |
| Myrcene | 1.86 |
| Alpha phellandrene | 0.23 |
| Alpha terpinene | 1.47 |
| Para-cymene | 12.65 |
| Beta phellandrene | 0.56 |
| Trans ocimene | 0.07 |
| Gamma terpinene | 15.45 |
| Sabinene trans hydrate | 0.19 |
| Linalool | 1.66 |
| Terpinen-4-ol | 0.61 |
| Thymol | 20.23 |
| Carvacrol | 38.61 |
| Beta caryophyllene | 1.88 |
| Alpha humulene | 0.1 |
| Caryophyllene oxide | 0.09 |
| TOTAL (%) | 97.69 | the major compounds of the EO are carvacrol (38.61%), thymol (20.23%), gamma terpinene (15.45%) and para-cymene (12.65%);

the minor compound is trans ocimene (0.07%);

there are 12 molecules common to the EO of oregano and the EO of rosewood: alpha pinene, camphene, myrcene, alpha terpinene, para-cymene, trans ocimene, gamma terpinene, linalool, terpineno-4-ol, beta caryophyllene, alpha humulene and caryophyllene oxide. These compounds are principally terpenes.

The percentages by weight of the major compounds of the essential oil of oregano were as follows:

para-cymene: 12.27% gamma terpinene: 16.10%, thymol: 18.65% carvacrol: 31.83%.

Conclusions:

The precise chemical composition of each EO was determined by gas chromatographic analysis (see Tables 1 and 2). Observation of the chemical composition of each EO revealed a very substantial qualitative difference if the number of major compounds was considered. Although the essential oil of rosewood has a larger number of different chemical molecules (approximately 62), it has one compound that is very much in the majority: linalool, more than 78% in the analyzed fraction. In contrast, the EO of oregano, with its 20 detected molecules, possessed four major molecules: carvacrol (38%), thymol (20%), gamma terpinene (15%) and para-cymene (12%). To this end, the EO of oregano is termed "mono-molecular" and the essential oil of oregano is termed "poly-molecular". It should also be noted that the EO of oregano is principally composed of mono-phenol (carvacrol and thymol), while the EO of rosewood is primarily constituted by terpenic alcohol (linalool).

Example 2

In the present work, the cytotoxicity of two essential oils was studied in particular: the essential oil of compact oregano (*Origanum compactum*, Lamiaceae family) and the essential oil of rosewood (*Aniba rosaeodora*, Lauraceae family) on human epidermal cells: the HaCat keratinocyte line (mutated at p53 and spontaneously immortalized), the A431 line (from spino-cellular carcinoma) as well as on normal human primary epidermal keratinocytes.

These three models were used to evaluate the potential biological effects of these two essential oils on normal epidermal cells mutated at p53 (that could be likened to pre-cancerous) and cancerous, the whole representing, to a certain extent, the various situations between healthy skin and skin with a risk of non-melanoma cancer.

Measurement of Cell Viability:

The inventors compared the cytotoxic effect of the essential oils on normal, mutated pre-cancerous (HaCat) and mutated cancerous (A431) keratinocytes.

Cell viability was determined by the MTT test after a 4 h and 20 h treatment with different concentrations of BO. This test (MTT) was based on the mitochondrial enzyme activity of dehydrogenase succinate. Each viability point is represented by three independent experiments (NHEK: normal human epidermal keratinocyte).

Figure 2:
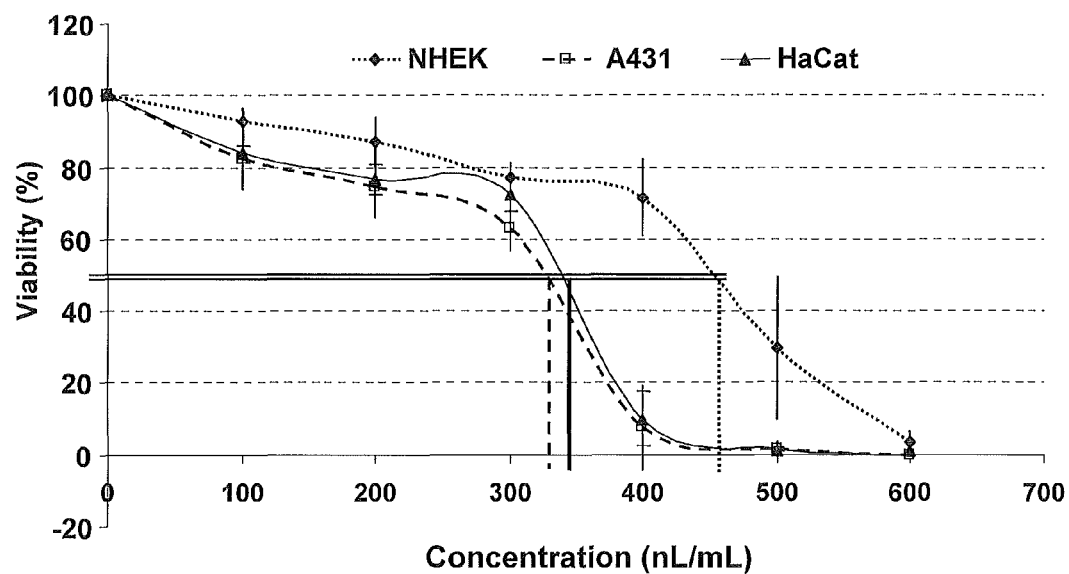
FIG. 2 represents the measurement of cell viability (MTT test) on A431, HaCat and NHEK cells treated for 4 h with the EO of rosewood. The double line (═) corresponds to the 50% lethal dose (LD50)

FIGS. 1 and 2 indicate that:
the EO of oregano is more toxic than the EO of rosewood, independent of time (comparison between 4 h and 20 h of treatment) and of the cell line used;
normal cells (NHEK) are more resistant than cancer cells (A431) and mutated pre-cancerous cells (HaCat) after 4 h of treatment;
the cytotoxicity profile is identical for the A431 and HaCat cells after 4 h of treatment (with the essential oils of oregano and rosewood).

Figure 3:
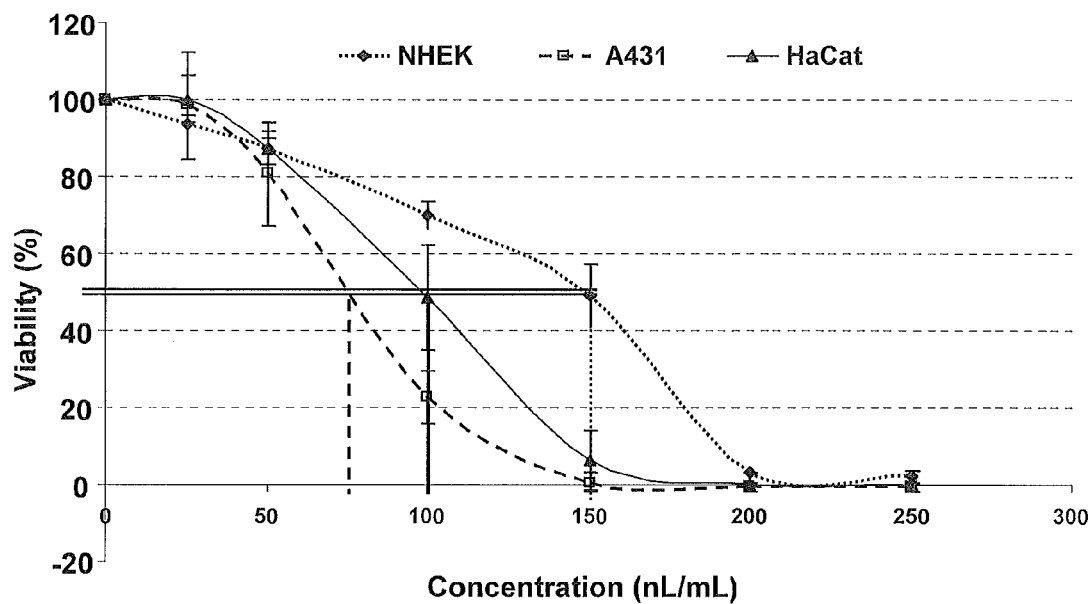
FIG. 3 represents the measurement of cell viability (MTT test) on A431, HaCat and NHEK cells treated for 20 h with the EO of oregano. The double line (═) corresponds to the 50% lethal dose (LD50)
Figure 4:
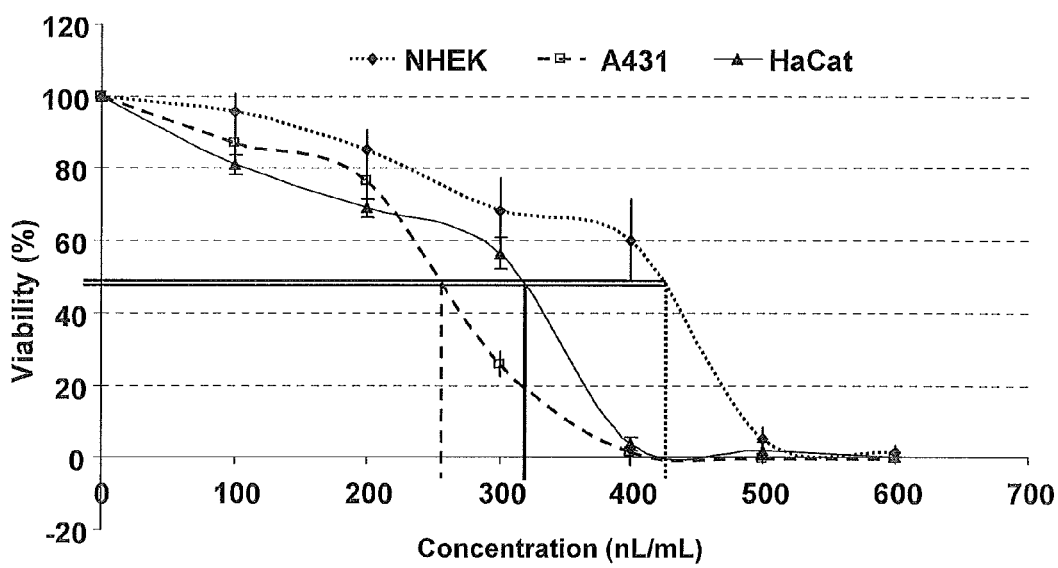
FIG. 4 represents the measurement of cell viability (MTT test) on A431, HaCat and NHEK cells treated for 20 h with the EU of rosewood. The double line (═) corresponds to the 50% lethal dose (LD50)

FIGS. 3 and 4 confirm that this difference in toxicity between the A431/HaCat cells and the NHEK cells was conserved after 20 h of treatment, although at this time a difference in sensitivity was observed between the HaCat and A431 cells.

These results demonstrate a targeted toxicity of the OEs for cancer cells and mutated pre-cancerous cells compared with normal cells at concentrations of 150 nL/mL and 400 nL/mL of the OE of oregano and of rosewood respectively.

Detection of Apoptosis:

Apoptosis is defined as the induction of characteristic biochemical events leading to programmed cell death. These characteristic events are, for example, translocation of a particular membrane phosphoplid (phosphatidylserine) of the internal plasma membrane, or activation of certain proteases (caspases) involved in the protein degradation process, leading to cell death.

The cell viability results brought to light a concentration for each EO where a difference is revealed in the sensitivity of cancer and mutated pre-cancerous cells compared with normal cells: 150 nL/mL for the EO of oregano and 400 nL/mL for the EO of rosewood. These concentrations will be used in the context of a 16 h treatment (4 h and 12 h treatments were also carried out).

Figure 5:
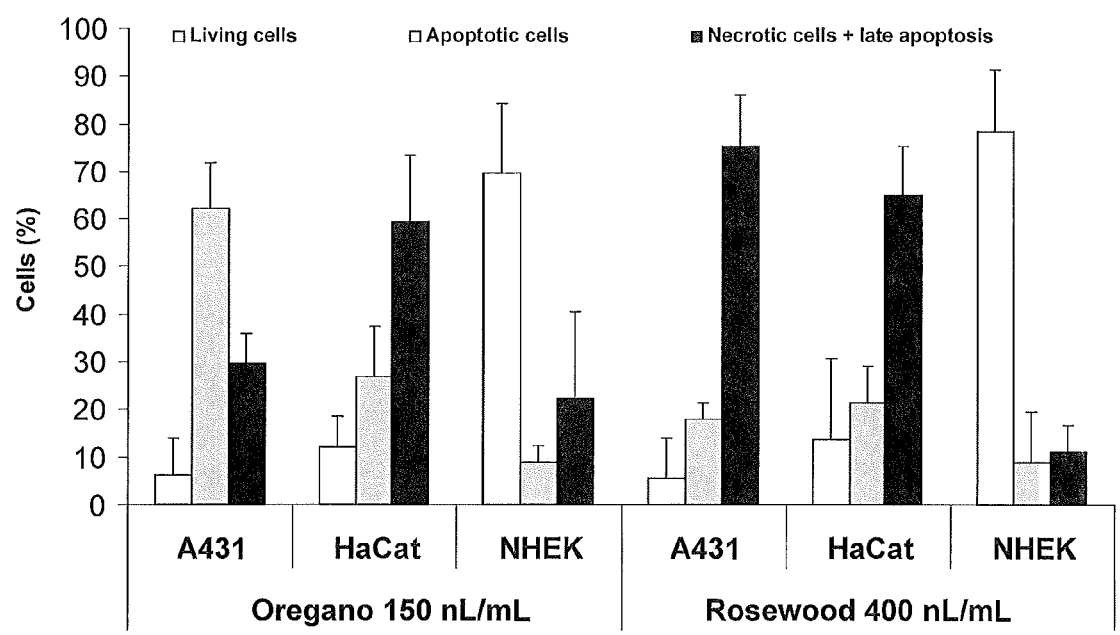
FIG. 5 represents the measurement of apoptosis (AV/PI test) in A431, HaCat and NHEK cells after 12 h of treatment with the EOs of oregano and rosewood.

FIG. 5 indicates that after 12 h of treatment:
there was a significantly higher viability for normal cells (NHEK: viability>70%) compared with the A431 cancer line and HaCat mutated pre-cancerous line (viability<15% in A431 and HaCat lines);
there was a substantial induction of apoptosis in the A431 cancer line (more than 60% of positive annexin V cells);
there was late apoptosis or necrosis in the mutated pre-cancerous HaCat cells.

These results confirm the higher sensitivity to the toxicity of the essential oils for the mutated pre-cancerous HaCat and cancerous A431 cells compared with the normal NHEK cells. They also bring to light an induction of cell death by apoptosis.

In order to confirm the induction of cell death by apoptosis by the essential oils, a second test based on the detection of the activity of caspases, a family of proteins specific to the apoptosis mechanism, was carried out on cells treated with the essential oils. Caspase activation is an earlier phenomenon than translocation of phosphatidylserine detected previously by annexin V. The principle of the test is based on the use of a substrate for these enzymes coupled to a fluorochrome. Cells in apoptosis, where the caspases are activated, will degrade the substrate and emit fluorescence. Non-apoptotic cells do not emit fluorescence. The fluorescence was measured by flow cytometry and fluorescence microscopy after 4 h of treatment with the essential oils.

Figure 6:
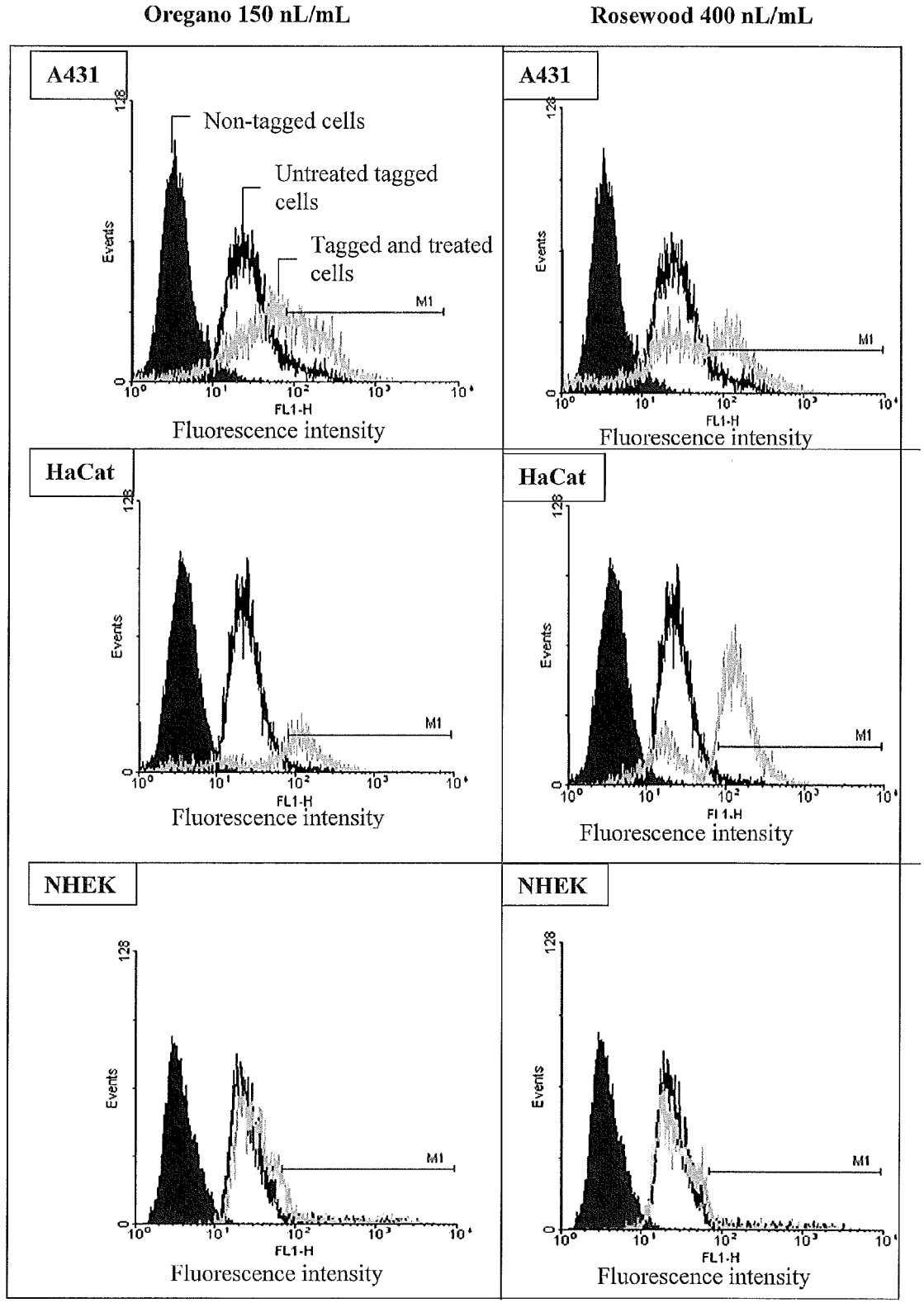
FIG. 6 represents the measurement of fluorescence (caspase activity) by flow cytometry. The non-tagged cells, the untreated tagged cells and the treated (by EO) and tagged cells are labeled.
Figure 7:
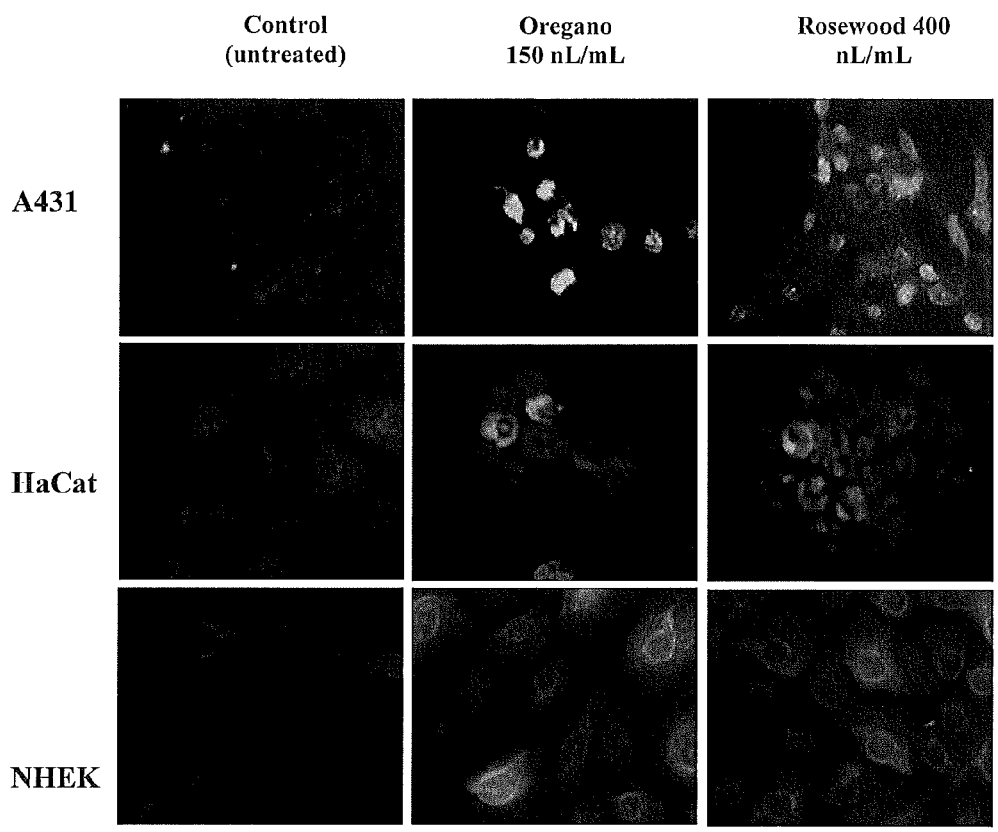
FIG. 7 represents the fluorescence (caspase activity) by fluorescence microscopy.

FIG. 6 shows up a displacement towards the right (and thus an increase in the fluorescence intensity) of the curve representing the cells treated with the essential oils compared with the curve representing the tagged but untreated cells in the A431 and HaCat cells only. This increase in fluorescence, which was confirmed by fluorescence microscopy (FIG. 7), indicates caspase activation and confirms the following:
induction of apoptosis in the cancer cells and HaCat cells by both essential oils, at the concentrations used;
that this induction is observed only in A431 and HaCat cells; the normal cells are thus more resistant than the cancer cells and mutated pre-cancerous cells for the same treatment with the essential oils of oregano and of rosewoods.

Effect of Essential Oils on Mitochondria

Figure 8:
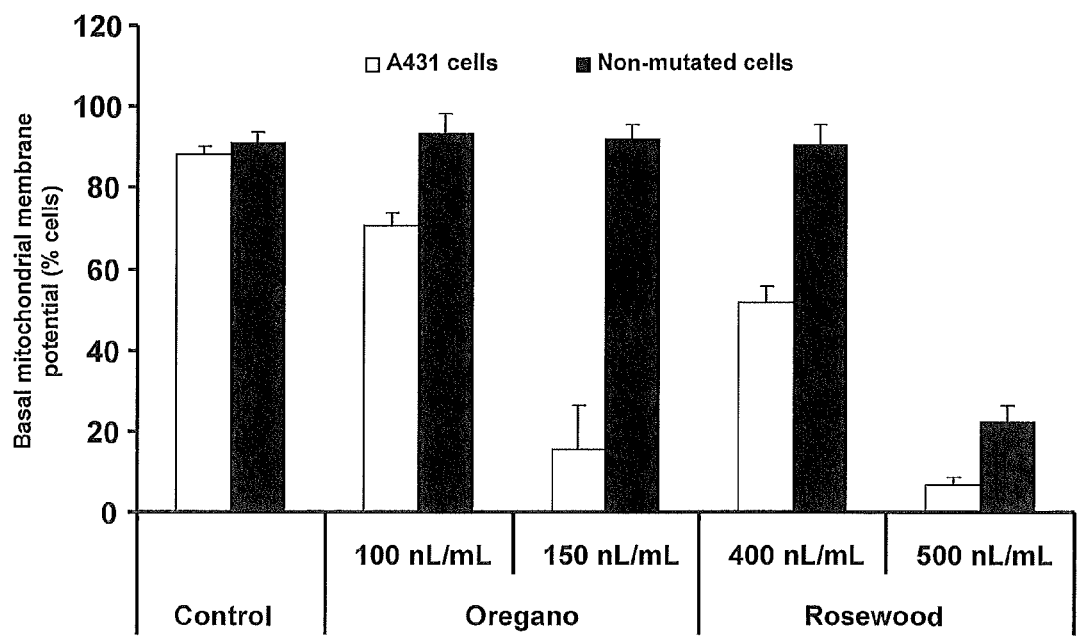
FIG. 8 illustrates the quantification of the number of A431 and HEK001 cells (non-mutated keratinocytes) that have undergone a drop in the mitochondrial membrane potential after 6 h of treatment with the EOs of oregano and rosewood.

After treatment with the essential oils of oregano and of rosewood, an analysis of the integrity of the mitochondrial membrane of the cancerous mutated A431 keratinocytes and non-mutated keratinocytes was carried out by flow cytometry (monitoring fluorescence linked to the accumulation of TMRM in the integrated mitochondrial membrane). It can be seen in FIG. 8 that in the selected concentration range, there was indeed a destabilizing effect on the mitochondria linked to treatment by the essential oils, but this effect was particularly marked in the A431 cells compared with the non-mutated keratinocytes. This impact on the mitochondria is very probably associated with the development of the apoptotic process (cause and/or consequence).

Figure 9:
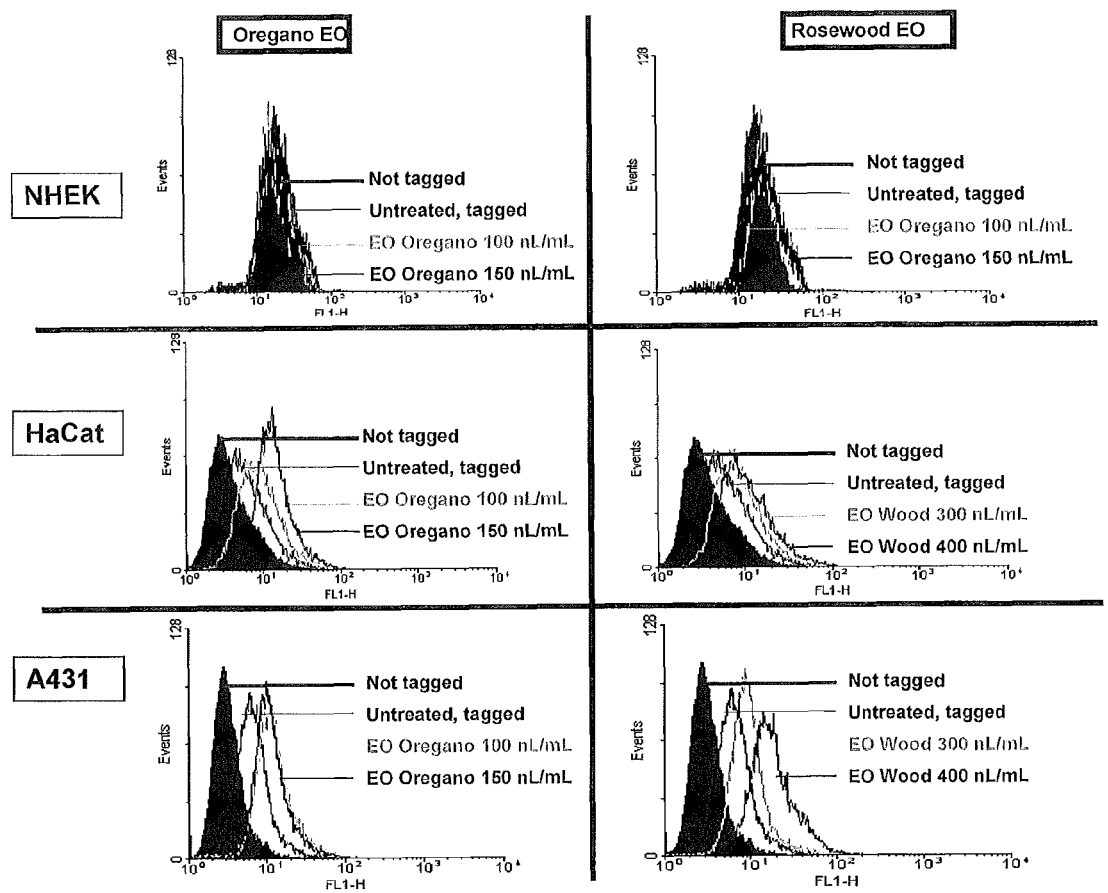
FIG. 9 illustrates the detection of oxidizing stress induced after incubation for 4 h with the EOs of oregano and rosewood in A431, HaCat and NHEK894 cells by measuring (flow cytometry) the fluorescence of the DHR 123 probe.

Intracellular Generation of Reactive Oxygen Species Following Treatment with Essential Oils One of the consequences of mitochondrial destabilization is the release of pro-oxidizing molecules into the cytosol; this phenomenon can be detected in flow cytometry by the DHR123 probe, which fluoresces in the case of an oxidizing stress. FIG. 9 shows the change in the number of fluorescent cells (which are thus subject to the generation of reactive oxygen species that can be detected by the DHR123) after various treatments with the essential oils. It will be seen that at the concentrations used, the normal keratinocytes were not affected, while a dose-dependent increase in the intracellular pro-oxidizing state could be detected in the mutated HaCat or A431 cells. Thus, the essential oils are capable of producing a significant and specific oxidizing stress in pre-cancerous or cancerous mutated keratinocytes, that stress probably being strongly implicated in the targeted cytotoxicity described in FIGS. 1 to 4.

Conclusions

The data presented here demonstrates a sensitivity to the cytotoxicity of the essential oils of oregano and of rosewood that is significantly higher in cancerous and mutated pre-cancerous human keratinocytes compared with normal keratinocytes.

The analysis of the mechanisms occurring has shown that this difference in sensitivity can be explained by the induction of death by apoptosis in the cancerous and mutated pre-cancerous cells, while the normal cells had cell viabilities of more than 70% for the same concentration of essential oil.

The molecular analysis shows that this specific toxicity by the essential oils involves modifications to mitochondrial integrity and the generation of an endogenic oxidizing stress. Thus, it can be envisaged that mutated pre-cancerous keratinocytes (in particular in keratoses or in zones of the skin damaged by UV) can be targeted by the essential oils and thus can specifically eliminate them.

Example 3

Measurement of the Pro-Apoptotic Activity of the Major Isolated Compounds of the Essential Oils of Oregano and Rosewood The essential oil of rosewood is composed of a primary molecule (more than 80%): linalool (terpene alcohol). The EO of compact oregano contains two primary compounds (monoterpenol): carvacrol and thymol, present in amounts of 40% and 20% respectively.

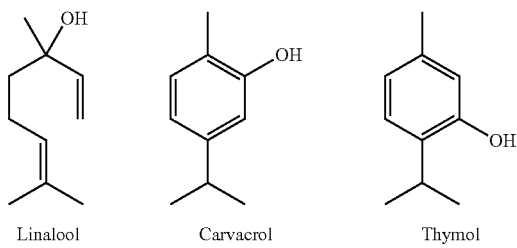

Linalool    Carvacrol    Thymol

These three molecules were incubated for 12 h with non-mutated immortalized keratinocytes (HEK001) and mutated cancerous keratinocytes (A431). The percentage of cells in apoptosis was measured by the annexin V/propidium iodide test. The concentrations of the molecules used were equal to those present during the treatments with the essential oils. Example: the concentration of linalool used here represents the equivalent of 80% of linalool present in the essential oil of rosewood. In fact, the linalool was used in a concentration of 320 nL/mL (see FIG. 10), i.e. 80% of 400 nL/mL of essential oil of rosewood, which is the concentration shown to be the most toxic for HaCat and A431 cells, while leaving a maximum of viable NHEK and HEK001 cells (see Example 2, conclusions on the section "Measurement of cell viability" and FIGS. 3 and 4 as well as the section "Detection of apoptosis" and FIG. 5). This was the same for the carvacrol and thymol of the essential oil of oregano.

Figure 10:
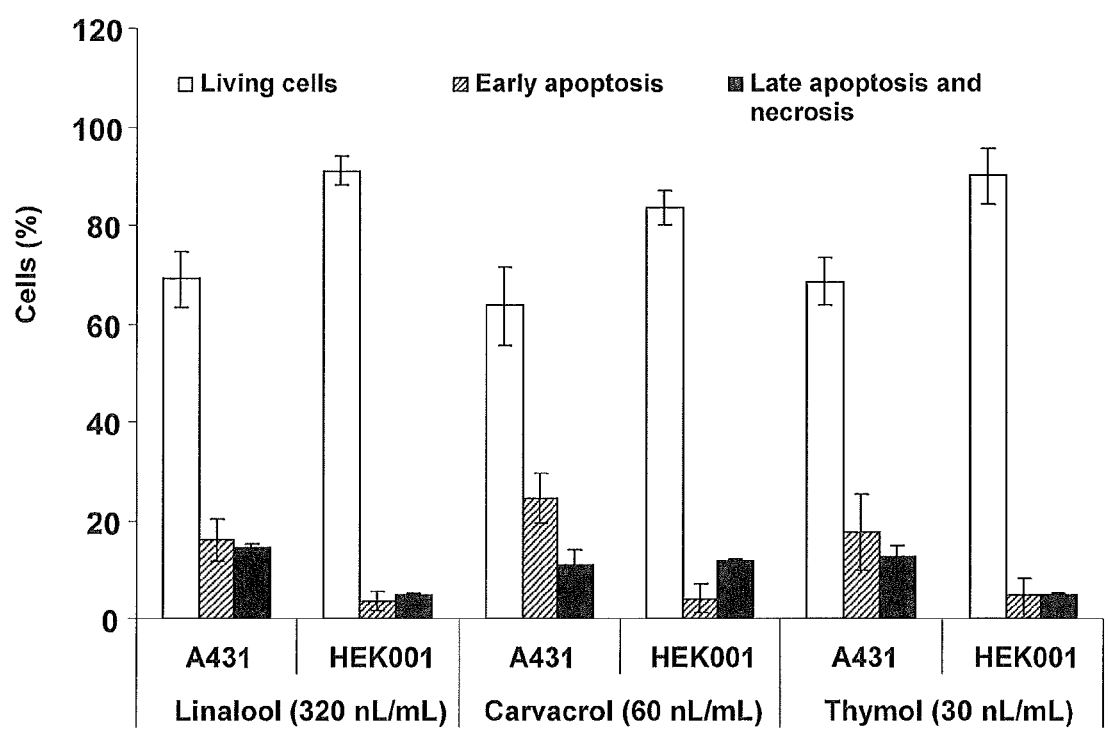
FIG. 10 represents the measurement of apoptosis (AV/PI test), in A431 and HEK001 cells (immortalized non-mutated keratinocytes) after 12 h of treatment with the following essential oil constituents: linalool, carvacrol and thymol.

The apoptosis results are presented in FIG. 10.

The results of this experiment, expressed as the % of cells—living, in apoptosis or in late apoptosis and necrosis, show the following:

lower cytotoxicity and pro-apoptotic cytotoxicity of the major molecules isolated compared with that induced by the essential oils in their complexity (70% apoptosis induced in cancer cells at the equivalent dose of the essential oil of oregano, i.e. 150 nL/mL). In fact, FIG. 5 highlights, for example, that more than 60% of the A431 cells are apoptotic after a treatment for 12 h with essential oil of oregano in a concentration of 150 nL/mL. FIG. 10, in contrast, shows that approximately only 25% of the A431 cells were apoptotic after 12 h of treatment with carvacrol in a concentration of 60 nL/mL (corresponding to 40% of 150 nL/mL) and approximately 15% of apoptotic cells with a treatment with 30 nL/mL thymol (corresponding to 20% of 150 nL/mL);

the viability of the non-mutated cells (HEK001) was higher than that observed in the mutated cells (A431). Preferential targeting of mutated cells was thus conserved.

This experiment shows that death by targeted apoptosis of mutated cancer cells is qualitatively conserved if the principal compounds of rosewood (linalool) or oregano (carvacrol and thymol) are used. In contrast, the cytotoxic efficacy is lower than with complex essential oils. Thus, synergistic effects with the other constituents probably exist.

This point is confirmed by the observation by the inventors that the mixture of several molecules isolated from the same essential oil reproduces the activity observed with the essential oil, the activity being higher than with simple addition of the activities of the isolated molecules taken separately.

Apparatus and Methods for Examples 2 and 3

Thirty six hours before the treatment, the cells were distributed into a 96-well plate ($5 \times 10^5$ cells/mL).

EO treatment solution: the essential oils were diluted to $\frac{1}{10}^{th}$ a first time in 100% ethanol. Next, a second dilution was carried out in culture medium in order to obtain the desired concentrations.

The viability measurement was carried out using the MTT test (1-(4,5-dimethylthiazol-2-yl)-3,5-diphenylformazan, Sigma-Aldrich). Briefly, after the desired treatment time, the treatment medium was replaced by a medium containing the MTT solution (0.25 µg/mL final concentration). The 96-well plate containing the cells was then incubated for 4 h at 37° C. before eliminating the MIT solution and adding 100 µl of DMSO. The absorbance measurement was then carried out at 540 nm after homogenizing the violet precipitate.

The measurement of the oxidizing stress was carried out using a DHR 123 fluorescent probe (Molecular Probe). After 4 h of treatment with the essential oils, the medium was eliminated and the cells were harvested (by trypsinization), centrifuged then rinsed in 4 mL of PBS 1×. The cells were then incubated for 30 min (27° C.) in culture medium containing the probe (5 µM). Before measuring the fluorescence by cytometry (excitation: 488 nm/emission: 530 nm), the cells were rinsed in 4 mL of PBS 1×, centrifuged and taken up in 0.5 mL of PBS.

Detection of Apoptosis:

Annexin V/Propidium Iodide Test:

One of the markers for apoptosis is the translocation of phosphatidyl-serine from the internal face towards the external face of the plasma membrane (translocation, allowing apoptotic bodies to be recognized and phagocyted by the macrophages).

The AV/PI test can be used to detect this event because of the affinity of the protein annexin V for phosphatidyl-serine. Propidium iodide, which targets DNA, can be used to distinguish early apoptotic cells from cells in late apoptosis and/or in necrosis.

After the desired treatment time, the medium was eliminated, the cells were harvested (by trypsinization), centrifuged and rinsed in 4 mL of PBS 1×. Tagging was carried out following the instructions of the manufacturer (Kit Vybrant, Molecular Probe). The cells were rapidly taken up in 100 µl of tagging buffer, to which 6 µl of annexin V and 3 µg/mL of propidium iodide per sample was added. The cells were then incubated for 30 min in the dark (at ambient temperature). Four hundred µL of tagging buffer was added before measuring the fluorescence of the annexin V (at 530 nm) and of the propidium iodide (at 610 nm).

Caspase Activity:

Caspase activity is a second marker of apoptosis. The caspase family encompasses the proteins principally involved in regulating cell death by apoptosis. The caspase activity was detected using a VAD (valine-alanine-aspartic acid) substrate coupled to a fluorochrome (FITC. Emission: 530 nm). Detection of this activity was carried out by following the instructions with the CasPACE™ kit (Promega). After treatment, the cells were harvested (by trypsinization), centrifuged and rinsed in 4 mL of PBS 1×. Next, the cells were incubated for 20 min in a culture medium containing the reagent (10 µM), 20 min in the dark and at ambient temperature. The cells were then rinsed twice in 4 mL of PBS 1× before being fixed for 30 min in a formalin solution. Before measuring the fluorescence by flow cytometry, the cells were rinsed (3 times 5 min) in PBS 1× then taken up in 0.5 mL of PBS.

Mitochondrial Permeabilization:

Permeabilization of mitochondrial pores is also an early marker of apoptosis. A fluorescent probe (TMRM: tetramethyl rhodamine methyl ester; Molecular Probe) becomes localized in the mitochondria, and will reduce in intensity when it migrates in the cytoplasm following opening of the mitochondrial pores. A fall in fluorescence is thus measured by flow cytometry.

After 4 h of treatment, the cells were trypsinated and rinsed in PBS 1× before they were incubated for 30 min at 37° C. in a culture medium containing the fluorescent probe (50 nM final). After this incubation, the cells were rinsed once for 5 min in PBS 1× then taken up in 0.5 mL of PBS before the cytometric measurement.

Example 4

Range of Essential Oil Concentration: Targeted Cytotoxicity

The ranges of concentrations of essential oil (as % of essential oil per volume of culture medium) for which the cytotoxicity property was observed to be preferentially induced in the mutated cells (HaCat and A431) compared with non-mutated cells (HEK001 and NHEK894) are:
from 0.0125% to 0.0175% for the essential oil of oregano;
from 0.035% to 0.045% for the essential oil of rosewood.

In these concentration ranges, the degrees of toxicity are twice as high in the mutated cells than in the non-mutated cells where the viability remains of the order of 60%.

Further, it should be pointed out that the studies have shown good skin penetration of the principal ingredients of the essential oils of rosewood and of oregano.

REFERENCES

Bakkali, F., et al. Antigenotoxic effects of three essential oils in diploid yeast (*Saccharomyces cerevisiae*) after treatments with UVC radiation, 8-MOP plus UVA and MMS. *Mutat. Res.* 606: 27-38, 2006.

Calcabrini, A., et al. Terpinen-4-ol, the main component of *Melaleuca alternifolia* (tea tree) oil inhibits the in vitro growth of human melanoma cells. *J. Invest. Dermatol.* 122: 349-360, 2004.

Cleaver J. E. and Crowley, E. UV damage, DNA repair and skin carcinogenesis. *Front Biosci.* 1: d1024-43, 2002.

Diaz, C., et al. Chemical composition of *Schinus molle* essential oil and its cytotoxic activity on tumour cell lines. *Nat. Prod. Res.* 22: 1521-1534, 2008.

Fusenig, N. E. and Boukamp, P. Multiple stages and genetic alterations in immortalization, malignant transformation, and tumor progression of human skin keratinocytes. *Mol. Carcinog.* 23: 144-158, 1998.

Gogvadze V. et al. Mitochondria in cancer cells: what is so special about them? *Trends Cell Biol.* 18: 165-173, 2008.

Itharat, A., et al. In vitro cytotoxic activity of Thai medicinal plants used traditionally to treat cancer. *J. Ethnopharmacol.* 90: 33-38, 2004.

Kaur, M., et al. Skin cancer chemopreventive agent, α-santalol, induces apoptotic death of human epidermoid carcinoma A431 cells via caspase activation together with dissipation of mitochondrial membrane potential and cytochrome C release. *Carcinogenesis* 26: 369-380, 2005.

Koba K., et al. In vitro cytotoxic activity of *Cymbopogon citratus* L. and *Cymbopogon nardus* L. essential oils from Togo. *Bangladesh J. Pharmacol.* 4: 29-34, 2009.

Kulms, D. and Schwarz, T. Molecular mechanisms of UV-induced apoptosis. *Photodermatol. Photoimmunol. Photomed.* 16: 195-201, 2000.

Kumar, A., et al. An essential oil and its major constituent isointermedeol induce apoptosis by increased expression of mitochondrial cytochrome C and apical death receptors in human leukaemia HL-60 cells. *Chem. Biol. Interact.* 171: 332-347, 2008.

Loizzo, M. et al. Antiproliferative effects of essential oils and their major constituents in human renal adenocarcinoma and amelanotic melanoma cells. *Cell Prolif.* 41: 1002-1012, 2008.

Margot, L. and Meunier, J. R. Skin DNA photodamage and its biological consequences. *J. Am. Acad. Dermatol.* 58: S139-S148, 2008.

Molassiotis, A., et al. Use of complementary and alternative medicine in cancer patients: a European survey. *Ann. Oncol.* 16: 655-663, 2005.

Mudgil, A. V., Segal, N., Andriani, F., Wang, Y., Fusenig, N. E., and Garlick, J. A. Ultraviolet B irradiation induces expansion of intraepithelial tumor cells in a tissue model of early cancer progression. *J. Invest. Dermatol.* 121: 191-197, 2003.

Ortonne, J. P. From actinic keratosis to squamous cell carcinoma. *Br. J. Dermatol.* 146 Suppl 61: 20-23, 2002.

Sharma, P. R., et al. Anticancer activity of an essential oil from Cymbopogon flexuosus. *Chem. Biol. Interact.* 2008.

Taguchi, M., et al. Aberrations of the tumor suppressor p53 gene and p53 protein in solar keratosis in human skin. *J. Invest. Dermatol.* 103: 500-503, 1994.

Verma, M., et al. Induction of mitochondrial-dependent apoptosis by an essential oil from *Tanacetum gracile*. *Planta Merl*. 74: 515-520, 2008.

Wischermann, K., et al. UVA radiation causes DNA strand breaks, chromosomal aberrations and tumorigenic transformation in HaCaT skin keratinocytes. *Oncogene* 27: 4269-4280, 2008.

The invention claimed is:

1. A method for the targeted treatment of keratoses in the transformation phase, of pre-cancerous or cancerous keratinocytes or of carcinoma originating from the transformation of keratoses, in human beings, comprising applying a composition comprising an essential oil extracted from plants of the genus *Origanum* or *Aniba*, or comprising at least one of the constituents of the essential oils of *Origanum compactum* or of *Aniba rosaeodora* selected from thymol, carvacrol, and linalool.

2. The method according to claim 1, wherein said composition comprises the essential oil of *Origanum compactum* or of *Aniba rosaeodora*.

3. The method according to claim 1, wherein the cumulative proportions of linalool, thymol, and carvacrol in said composition are more than 15% by weight.

4. The method according to claim 1, wherein said composition comprises at least 15% by weight of the essential oil of *Origanum compactum* or of *Aniba rosaeodora* or of linalool, thymol, or carvacrol.

5. The method according to claim 1, wherein said composition comprises vegetable oils.

6. The method according to claim 1, wherein said composition is applied topically to the skin.

7. The method according to claim 1, wherein said keratoses are actinic keratoses.

8. The method according to claim 1, wherein said carcinoma is a spino-cellular carcinoma or a baso-cellular carcinoma.

9. The method according to claim 1, wherein said keratoses, cancerous keratinocytes, or carcinoma are characterized by cells carrying mutations in the p53 protein.

10. The method according to claim 1, wherein said composition is to be applied in association with another treatment against keratoses.

11. The method according to claim 1, wherein said composition is to be applied before, during, after, or alternating with another treatment against keratoses.

12. The method according to claim 1, wherein said targeted treatment is free of deleterious effects on normal keratinocytes.

13. The method according to claim 1, inducing a preferential cytotoxicity in hyperproliferative keratinocytes compared with non-hyperproliferative keratinocytes.

14. The method according to claim 1, wherein the essential oil or the constituent constitutes an active principle of the composition.

15. The method according to claim 1, wherein the cumulative proportions of linalool, thymol, and carvacrol in said composition are more than 20% by weight.

16. The method according to claim 1, wherein said composition comprises at least 20% by weight of the essential oil of *Origanum compactum* or of *Aniba rosaeodora* or of linalool, thymol, or carvacrol.

17. The method according to claim 1, wherein said composition is to be applied in association with a chemotherapy or a dynamic phototherapy (DPT).

18. The method according to claim 1, wherein said composition is to be applied before, during, after, or alternating with a treatment by chemotherapy or by dynamic phototherapy.

* * * * *